United States Patent [19]

Bochis et al.

[11] Patent Number: 4,590,201
[45] Date of Patent: May 20, 1986

[54] 5-AMINO OR SUBSTITUTED AMINO 1,2,3-TRIAZOLES

[75] Inventors: Richard J. Bochis, East Brunswick; John C. Chabala, Westfield; Michael H. Fisher, Ringoes, all of N.J.

[73] Assignee: Merck & Co., Inc., Rahway, N.J.

[21] Appl. No.: 576,301

[22] Filed: Feb. 2, 1984

[51] Int. Cl.$^4$ .................. C07D 249/06; A01N 43/36
[52] U.S. Cl. ...................................... 514/359; 548/255
[58] Field of Search ....................... 548/255; 424/249; 514/359

[56] References Cited

U.S. PATENT DOCUMENTS 3,948,885  4/1976  Witkowski et al. ................. 548/255
4,341,700  7/1982  Matzinger .......................... 548/255

FOREIGN PATENT DOCUMENTS 1511195  5/1978  United Kingdom .

OTHER PUBLICATIONS

Tennant: Chem. of Polyazohetero. Cupts VI Dimrotarearray. of Triazoles, CA 74 (23): 125581z (1971).
Peters et al; Inhibiting Pavine Biosynthesis Ing 4(5) Aminoamidozoles-5(4)Carboxamides, CA 68 (23): 103631q (1968).
DeSehimo et al: Synthesizing Pharmacological Activity of 9-aryl-Sazadenine Inv. Farmaco Ed-Sci., 35(4) 308-323 (1980).
Da Settino et al II: 1-2-3 Triazole Deriv. of Arylalkanoic Acids: Farmaco Ed. Sci. 34(5) 371-382 (1979).
Ferlauto, R.: Controlling Coccidiosis in Poultry Employing Triazole Deriv., CA 75(13) 87461w (1971).
Levine, H. B.: Comparison of Oral Treatments with Bay in 7133 Ketaconozole, CA 100(17): 132137t (1984).
Ajinomoto Co. Inc.: Triazole-4-Carboxylic Acids, CA 94(1): 4027(c) (1980).
Albert, A. IV: 1,2,3 Triazole Analogs of 2-Aminobenzylamine, CA 73(15): 77154t (1970).
Albert, A. V: Dimroth Rearrangement Part XV: Catalysis by Methylamine Salts, CA 80(15): 82890d.
Itamader et al; Triazole Anticoccidium Agents: CA 83(15) 126969e (1975).
Calautti et al: New Coccideostatic Drugs of Iamino-9-H-1,2-4 Triazole Series, CA 76(17): 99572s.
Lucacchini et al—Effects of Subst. 1,2-3 Triazole on a Dinosine Duninore etc. Ital. J. Biochem. 28(3) 194-206 (1979).
Albert, A. I: V-Triazolo [4,5—d]pyrimidines: part 24—3 alkyl, Derw. CA 95 (17): 150600w (1981).
Albert, A. II: V-Triazolo Pyrimidines: Part 18—3 mm for Synthesizing 8-azupurinationes: CA 86(23): 171374e (1977).
Albert, A. III: V-Triazolo Pyrimidines: Part 16: Prep. of 6-Amino-8 Azaparines by Heating, CA 82(25): 170802y.

Primary Examiner—Glennon H. Hollrah
Assistant Examiner—D. L. Dinner
Attorney, Agent, or Firm—David L. Rose; Michael C. Sudol, Jr.; Mario A. Monaco

[57] ABSTRACT

Novel 5-amino or substituted amino 1,2,3-triazoles are disclosed as having anticoccidial activity. The compounds are useful for controlling coccidiosis when administered in minor quantities to animals, in particular to poultry, usually in admixture with animal sustenance.

15 Claims, No Drawings

5-AMINO OR SUBSTITUTED AMINO 1,2,3-TRIAZOLES

BACKGROUND OF THE INVENTION

This invention relates to new chemical compounds and the method of the preparation of the same. It relates further to the use of such new compounds for treating and preventing coccidiosis. This invention still more particularly relates to novel 5-amino and substituted amino 1,2,3-triazole compounds and substituted derivatives thereof and the use of the same in the control and treatment of coccidiosis.

Coccidiosis is a wide-spread poultry disease which is produced by infections of protozoa of the genus Eimeria which causes severe pathology in the intestines and ceca of poultry. Some of the most significant of these species are *E. tenella*, *E. acervulina*, *E. necatrix*, *E. brunetti*, *E. maxima*, *E. mitis*, *E. mivati*, *E. hagani* and *E. praecox*. This disease is generally spread by the birds picking up the infectious organism in droppings on contaminated litter or ground or by way of food or drinking water. The disease is manifested by hemorrhage, accumulation of blood in the ceca, passage of blood to the droppings, weakness and digestive disturbances. The disease often terminates in the death of the animal but the fowl which survive severe infections have had their market value substantially reduced as a result of the infection. Coccidiosis is therefore a disease of great economic importance and extensive work has been done to find new and improved methods for controlling and treating coccidial infections in poultry.

SUMMARY OF THE INVENTION

This invention is based on the discovery that certain novel 5-amino and substituted amino 1,2,3-triazoles as well as substituted derivatives thereof have a surprisingly and unexpectedly high degree of activity against coccidiosis of poultry. Administration of a small amount of at least one of these compounds preferably by combination with poultry feed is effective in preventing or greatly reducing the incidence of coccidiosis. The compounds are effective against both the cecal form (caused principally by *E. tenella*) and the intestinal forms (principally caused by *E. acervulina*, *E. brunetti*, *E. maxima* and *E. necatrix*). The coccidiostats of this invention are particularly effective against the species that cause cecal damage in addition to preventing the pathology caused by the coccidia.

The instant compounds are also active against *Eimeria spp*, in other animals.

The 1,2,3-triazole derivatives may be prepared by reacting appropriately substituted nitriles with appropriately substituted azides in the presence of a base in a suitable reaction medium to obtain such novel 5-amino-1-substituted-1,2,3-triazoles.

The novel 1,2,3-triazole derivatives of this invention may also be prepared by reacting an appropriately substituted halide and a 1-unsubstituted 1,2,3-triazole compound in the presence of a base in a suitable reaction medium to obtain such novel 5-amino or substituted amino 1-substituted 1,2,3-triazoles.

The novel 1,2,3-triazole derivatives of this invention may also be prepared by reaction of a 1-substituted 5-amino-1,2,3-triazole compound with an appropriately substituted halide in the presence of a base in a suitable reaction medium to obtain such novel 1-substituted-5-substituted amino 1,2,3-triazoles.

It is therefore a primary object of this invention to provide novel 5-amino or substituted amino 1,2,3-triazoles with appropriate substitutions at the 1, 4 and 5-positions which are useful in the control of coccidiosis. Still another object of this invention is to provide novel feed compositions useful for the prevention and suppression of coccidiosis. A further object of this invention is to provide a new and useful method for the control of coccidiosis in poultry which comprises administering to the poultry minor amounts of the anticoccidial substance of this invention. A still further object of this invention is to provide a method and alternate methods for preparing novel 5-amino and substituted amino 1,2,3-triazoles. These and further objects of this invention will become apparent from reading the following description.

DESCRIPTION OF THE INVENTION

The novel compounds of this invention are best realized in the following structural formula:

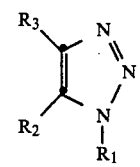

wherein:

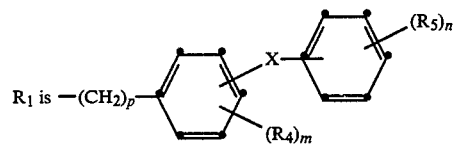

wherein p is 0 to 2; m is 0 to 4; and n is 0 to 5; X is O, S, SO, $SO_2$, CO, CHCN, $CH_2$ or $C=NR_6$ where $R_6$ is hydrogen, loweralkyl, hydroxy, loweralkoxy, amino, loweralkylamino, diloweralkylamino or cyano; and, $R_4$ and $R_5$ are independently halogen, cyano, trifluoromethyl, loweralkanoyl, nitro, loweralkyl, loweralkoxy, carboxy, carbalkoxy, trifluoromethoxy, acetamido, loweralkylthio, loweralkylsulfinyl, loweralkylsulfonyl, trichlorovinyl, trifluoromethylthio, trifluoromethylsulfinyl, or trifluoromethylsulfonyl;

$R_2$ is amino, mono or diloweralkyl amino, acetamido, acetimido, ureido, formamido, formimido or guanidino; and $R_3$ is carbamoyl, cyano, carbazoyl, amidino or N-hydroxycarbamoyl.

The preferred compounds of the instant invention are realized in the foregoing structural formula wherein:
p is 1; X is O, S, SO, $SO_2$, CO or $C=NR_6$ wherein $R_6$ is hydrogen, hydroxy, methoxy or cyano;
$R_4$ is fluoro, chloro, bromo, methyl, trifluoromethyl, cyano, carbomethoxy, trifluoromethoxy, trifluoromethylthio, or trichlorovinyl;
$R_5$ is halogen, methyl, trifluoromethyl, cyano, carbalkoxy, or trichlorovinyl;
$R_2$ is amino and
$R_3$ is carbamoyl.

The most preferred compounds of the instant invention are realized in the foregoing structural formula wherein p is 1; X is S, SO, SO$_2$, CO or C=NR$_6$ wherein R$_6$ is hydrogen, hydroxy, methoxy, or cyano;

R$_4$ is mono- or di-substituted ortho to X and are independently fluoro, chloro, methyl, trifluoromethyl, cyano or carbomethoxy;

R$_5$ is 1 to 3 substituents meta and/or para to X and which are independently fluoro, chloro, methyl, cyano, carbomethoxy or trichlorovinyl;

R$_2$ is amino; and

R$_3$ is carbamoyl.

Examples of preferred compounds of this invention are:

5-amino-1-[4-(4-chlorobenzoyl)-3,5-dichlorobenzyl]-1,2,3-triazole-4-carboxamide, 5-amino-1-[4-(4-chlorophenylthio)-3,5-dichlorobenzyl]-1,2,3-triazole-4-carboxamide, 5-amino-1-[4-(4-chlorophenylsulfinyl)-3,5-dichlorobenzyl]-1,2,3-triazole-4-carboxamide, 5-amino-1-[4-(4-chlorobenzoyl)-3-chloro-5-methylbenzyl]-1,2,3-triazole-4-carboxamide, 5-amino-1-[4-(4-chlorobenzoyl)-3,5-dimethylbenzyl]-1,2,3-triazole-4-carboxamide, 5-amino-1-[4-(4-trifluoromethylbenzoyl)-3-chloro-5-methylbenzyl]-1,2,3-triazole-4-carboxamide, 5-amino-1-[4-(4-chlorobenzoyl)-3-trifluoromethylbenzyl]-1,2,3-triazole-4-carboxamide, 5-amino-1-[4-(3,4-dichlorobenzoyl)-3,5-dichlorobenzyl]-1,2,3-triazole-4-carboxamide, 5-amino-1-(4-[1-(3-methylbenzimino)]-3,5-dichlorobenzyl)-1,2,3-triazole-4-carboxamide, 5-amino-1-[4-(4-fluorobenzoyl)-3-chloro-5-methylbenzyl]-1,2,3-triazole-<-carboxamide.

In the instant invention the term "loweralkyl" is intended to include those alkyl groups containing from 1 to 3 carbon atoms. Exemplary of such groups are methyl, ethyl, propyl and isopropyl.

The term "loweralkoxy" is intended to include those alkoxy groups containing from 1 to 3 carbon atoms. Exemplary of such groups are methoxy, ethoxy, propoxy, and isopropoxy.

The term "loweralkanoyl" is intended to include those alkanoyl groups containing 1 to 3 carbon atoms exemplified by formyl, acetyl, and propionyl.

The compounds of the instant invention may be prepared by any one of several processes. The most general process is outlined in the following reaction scheme.

A procedure for preparing the instant compounds is realized in the following reaction scheme:

Reaction Scheme I:

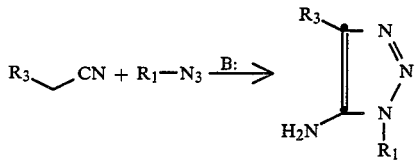

wherein R$_3$-methylene substituted nitrile is allowed to react with an R$_1$ substituted azide in the presence of a base to provide the desired 5-amino-1-substituted-1,2,3-triazole. The reaction is carried out in solvents such as aromatic hydrocarbons, lower alkanols, dimethylformamide, dimethylsulfoxide or hexamethylphosphortriamide. The base may be any alkali metal or alkaline earth hydroxide, alkoxide or hydride such as sodium ethoxide, potassium t-butoxide, magnesium ethoxide, sodium hydroxide or sodium hydride, chosen to be compatible with the reaction solvent. Generally the reaction is conducted at from −40° C. to 100° C. and is complete in from 15 mm to 48 h. The product of the reaction is isolated by techniques known to those skilled in the art.

Reaction Scheme II

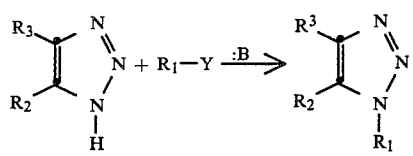

wherein Y is a halogen, preferably chlorine or bromine. In the foregoing reaction a 1-unsubstituted but otherwise appropriately substituted 1,2,3-triazole is reacted with a halogen substituted R$_1$ group in the presence of a base to prepare the desired 1-substituted 1,2,3-triazole. The reaction is carried out in a solvent which may be any polar aprotic organic solvent such as dimethylformamide, dimethylsulfoxide, acetonitrile, dioxane, and the like in the presence of a base. The base may be any non-nucleophilic organic or inorganic base. Suitable inorganic bases are alkali metal bases, such as sodium and potassium carbonates, phosphates, bicarbonates and hydroxides, or sodium hydride, chosen for compatibility with the reaction solvent. Suitable organic bases are tertiary amines such as trialkyl substituted amines and cyclic aromatic amines such as pyridine or collidine. The reaction rate varies greatly with the nature of the proposed substituent at the R$_1$ position, the base being used in the reaction and the solvent. Very reactive substituent and base combinations may be complete in as little as ten minutes and at the other extreme the reaction may take as long as two weeks. Most reactions are however complete in from 1 to 100 hours. The reaction is carried out at a temperature of from room temperature to 100° C. or to the reflux temperature of the solvent system being used. The products of the reaction are isolated using techniques known to those skilled in the art.

The starting materials used for the preparation of the instant compounds are prepared using techniques known to those skilled in the art. A particularly advantageous procedure for the preparation of the benzophenone starting materials, those wherein X is a carbonyl, involves a lithiation reaction of a benzene wherein a substituent of halogen or methoxy is ortho to the position of attachment of the benzoyl moiety and a methyl or substituted silyl is present.

The reaction is carried out using an organolithium reagent such as n-butyllithium in an inert solvent at temperatures of from 0° to −80° C. The lithiation reaction is substantially complete in from 30 minutes to 4 hours. The lithiated intermediate is allowed to react in situ with an acylating agent such as a substituted benzoyl chloride, benzoate ester, or nitrile. This phase of the reaction is conducted at from −80° to 25° C. and is complete in from 15 minutes to 6 hours. The product is isolated using known techniques.

The novel compounds of this invention are orally administered to poultry for the control and prevention of coccidiosis. Any number of conventional methods are suitable for administering the coccidiostats of this invention to poultry, as for example, they may be given in the poultry feed. The actual quantity of the coccidiostats administered to the poultry in accordance with this invention will vary over a wide range and be adjusted to individual needs, depending upon species of the coccidia involved and severity of the infection. The limiting criteria are that the minimum amount is sufficient to control coccidiosis and the maximum amount is such that the coccidiostat does not cause any undesirable effects.

A feed typically contains from about 0.0001 to about 0.2 percent, preferably from about 0.001 to about 0.1 percent, by weight of one of the coccidiostats of this invention. The optimum levels will naturally vary with the specific compound utilized and species of Eimeria involved, and can be readily determined by one skilled in the art. Levels of the 5-amino and substituted amino 1,2,3-triazoles of this invention, in poultry feed of from about 0.001 percent to about 0.1 percent by weight of the diet are especially useful in controlling the pathology associated with E. tenella, as well as the intestinal dwelling species.

Depending on the compound employed, levels as low as 0.0001 percent possess the novel effects of reducing the number of oocysts passed in the droppings of infected chickens.

The quantity or concentration of a novel coccidiostat of this invention in any admixture in which it is administered to the poultry will, of course, vary in accordance with the type of admixture utilized.

Of the various methods of administering the coccidiostats of this invention to poultry, they are most conveniently administered as a component of a feed composition. The novel coccidiostats may be readily dispersed by mechanically mixing the same in finely ground form with the poultry feedstuff, or with an intermediate formulation (premix) that is subsequently blended with other components to prepare the final poultry feedstuff that is fed to the poultry. Typical components of poultry feedstuffs include molasses, fermentation residues, corn meal, ground and rolled oats, wheat shorts and middlings, alfalfa, clover and meat scraps, together with mineral supplements such as bone meal and calcium carbonate and vitamins.

The following non-limiting examples will serve to further illustrate the instant invention.

EXAMPLE 1

4-(4-Chlorobenzoyl)toluene

An 80° C. stirred solution of p-toluoyl chloride (10.0 g, 64.7 mmol) in chlorobenzene (15 ml) was treated in portions with aluminum chloride (8.63 g, 64.7 mmol) over 20 minutes. The mixture was stirred 15 hours at 80° C., cooled, and quenched by addition of ice-water and concentrated hydrochloric acid (10 ml). The mixture was extracted twice with diethyl ether and once with a small volume of dichloromethane. The combined extracts were washed with water, 10% (w/v) aqueous sodium hydroxide, and water, dried over anhydrous magnesium sulfate, and evaporated to dryness under vacuum. The residue was dissolved in boiling n-hexane, treated with activated charcoal, and filtered hot. The filtrate was cooled and the product was collected by filtration and dried to provide 7.57 g (51%) of 4-(4-chlorobenzoyl) toluene, m.p. 122°–123° C.

EXAMPLE 2

4-(4-Chlorobenzoyl)benzyl bromide

A mixture of 4-(4-chlorobenzoyl)toluene (5.48 g, 23.8 mmol), dibenzoylperoxide (100 mg, 0.413 mmol), and N-bromosuccinimide (4.56 g, 25.6 mmol) in carbon tetrachloride (70 ml) was refluxed for 2 hours, cooled, filtered, and evaporated under vacuum. The residue was chromatographed on silica gel (1 kg) eluted with 97:3 (v/v) hexane-ethyl acetate using a preparative high-performance liquid chromatograph. Appropriate fractions were pooled and evaporated under vacuum to provide 4.61 g (63%) of 4-(4-chlorobenzoyl)benzyl bromide, m.p. 103°–104° C.

EXAMPLE 3

4-(4-Chlorobenzoyl)benzyl azide

A mixture of 4-(4-chlorobenzoyl)benzyl bromide (4.36 g, 14.1 mmol) and sodium azide (1.32 g, 20.3 mmol) in ethanol (40 ml) was refluxed 5 hours, cooled to ambient temperature, and stirred 16 hours. The mixture was filtered and the solids were washed twice with ethanol and once with diethyl ether. The combined filtrate and washes were evaporated under vacuum to provide 3.63 (95%) of 4-(4-chlorobenzoyl)benzyl azide, m.p. 71°–73° C.

EXAMPLE 4

5-Amino-1-(4-[4-chlorobenzoyl]benzyl)-1,2,3-triazole-4-carboxamide

To a suspension of 2-cyanoacetamide (527 mg, 6.27 mmol) in ethanol (20 ml) was added sodium methoxide (330 mg, 6.11 mmol). The mixture was refluxed 15 minutes, cooled slightly, and 4-(4-chlorobenzoyl)benzyl azide (1.24 g, 4.56 mmol) was added. The mixture was refluxed 2 hours, cooled to ambient temperature, and filtered. The filtrate was evaporated under vacuum and the residue was triturated with hot 19:1 (v/v) dichloromethane-methanol (50 ml) and filtered. The remaining solid was triturated with hot methanol (3 ml), filtered, and dried at 60° C. under vacuum to provide 182 mg (11%) of 5-amino-1-(4-[4-chlorobenzoyl]benzyl)-1,2,3-triazole-4-carboxamide, m.p. 229°–231° C.

EXAMPLE 5

3-(4-Chlorobenzoyl)toluene

A stirred solution of m-toluoyl chloride (10.0 g, 64.7 mmol) in chlorobenzene (13.2 ml) at 80° C. was treated with aluminum chloride (8.63 g, 64.7 mmol) in portions over 30 minutes. The mixture was stirred 15 hours at 80° C., cooled to ambient temperature, stirred 16 hours, and quenched by addition of ice and concentrated hydrochloric acid (5.0 ml). The mixture was extracted three times with dichloromethane, and the combined extracts were washed with water, dried over anhydrous magnesium sulfate, and evaporated under vacuum. The residue was dissolved in boiling n-hexane, treated with activated charcoal, filtered, and cooled. The product was filtered and dried to provide 9.15 g of 3-(4-chlorobenzoyl) toluene. The filtrate was concentrated under vacuum and filtered to provide an additional 0.28 g of product. Total yield was 9.42 g (63%), m.p. 103°–105° C.

EXAMPLE 6

3-(4-Chlorobenzoyl)benzyl bromide

A mixture of 3-(4-chlorobenzoyl)toluene (5.48 g, 23.7 mmol) and dibenzoylperoxide (100 mg, 0.413 mmol) in carbon tetrachloride (45 ml) was treated with N-bromosuccinimide (4.65 g, 26.7 mmol) and refluxed 2.5 hours. The mixture was filtered while hot and slowly cooled to ambient temperature. The precipitate was collected by filtration, washed twice with carbon tetrachloride, and dried under vacuum to provide 4.2 g (57%) of 3-(4-chlorobenzoyl)benzyl bromide, m.p. 123°–125° C.

EXAMPLE 7

3-(4-Chlorobenzoyl)benzyl azide

A mixture of 3-(4-chlorobenzoyl)benzyl bromide (4.2 g, 13.6 mmol) and sodium azide (1.32 g, 20.3 mmol) in ethanol (40 ml) was refluxed for 5 hours, cooled to ambient temperature, and kept 16 hours. The mixture was filtered and the solids were washed twice with ethanol. The combined filtrate and washes were evaporated to dryness under vacuum and the residue was treated with diethyl ether and filtered. The filtrate was evaporated to dryness under vacuum and dried to provide 3.7 g (100%) of 3-(4-chlorobenzoyl)-benzyl azide, m.p. 43°–45° C.

EXAMPLE 8

5-Amino-1-(3-[4-chlorobenzoyl]benzyl)-1,2,3-triazole-4-carboxamide

To a stirred solution of sodium (0.147 g, 6.41 mmol) in ethanol (20 ml) under nitrogen atmosphere was added 2-cyanoacetamide (539 mg, 6.41 mmol) and the mixture was refluxed 10 minutes. The mixture was cooled slightly, 3-(4-chlorobenzoyl)benzyl azide (1.34 g, 4.93 mmol) was added, and the mixture was refluxed 1 hour. The mixture was cooled to 0° C. and filtered. The product was washed with ice cold ethanol (2×5 ml), water (3×5 ml), ice cold ethanol (2×5 ml) and diethyl ether (10 ml), and dried at 50° C. for 3 hours under vacuum to provide 1.09 g (62%) of 5-amino-1-(3-[4-chlorobenzoyl]benzyl)-1,2,3,-triazole-4-carbomxamide, m.p. 206°–207.5° C.

EXAMPLE 9

4-(4-Chlorobenzoyl)-3-chlorotoluene

A stirred 80° C. solution of 2-chloro-4-methylbenzoyl chloride (6.6 g, 39 mmol) in chlorobenzene (10 ml) was treated with aluminum chloride (5.14 g, 38.5 mmol) in portions over 15 minutes. The mixture was stirred 15 hours at 80° C., cooled, quenched by addition of ice and concentrated hydrochloric acid (5 ml), and extracted three times with diethyl ether. The combined extracts were washed with water and saturated aqueous sodium bicarbonate, dried over anhydrous magnesium sulfate, and evaporated under vacuum. The residue was chromatographed on a column of silica gel (250 g) eluted with 7:3 (v/v) n-hexane-dichloromethane to provide 7.9 g (76%) of 4-(4-chlorobenzoyl)-3-chlorotoluene, m.p. 58°–60.5° C.

EXAMPLE 10

4-(4-Chlorobenzoyl)-3-chlorobenzyl bromide

A stirred refluxing solution of 4-(4-chlorobenzoyl)-3-chlorotoluene (2.65 g, 9.99 mmol) and dibenzoylperoxide (100 mg, 0.413 mmol) in benzene (100 ml) was treated in portions with an intimate mixture of N-bromosuccinimide (2.2 g, 12. mmol) and dibenzoylperoxide (100 mg, 0.413 mmol). The mixture was refluxed 1.5 hours, cooled, and filtered. The filtrate was evaporated under vacuum, triturated with diethyl ether (100 ml), and filtered. The filtrate was evaporated under vacuum and the residue was chromatographed on silica gel (500 g) eluted with 97:3 (v/v) n-hexane-ethyl acetate using a preparative highperformance liquid chromatograph to provide 1.69 g (49%) of 4-(4-chlorobenzoyl)-3-chlorobenzyl bromide, m.p. 88°–90° C.

EXAMPLE 11

4-(4-Chlorobenzoyl)-3-chlorobenzyl azide

A stirred suspension of 4-(4-chlorobenzoyl)-3-chlorobenzyl bromide (1.60 g, 4.65 mmol) and potassium azide (0.715 g, 8.81 mmol) in ethanol (15 ml) was refluxed 5 hours, cooled to ambient temperature, and stirred 16 hours. The solids were filtered and washed twice with ethanol. The combined filtrate and washes were evaporated under vacuum, diluted with diethyl ether (40 ml), filtered, and evaporated under vacuum to provide 1.51 g (106% of theory) of 4-(4-chlorobenzoyl)-3-chlorobenzyl azide, m.p. 33°–33.5° C., suitable for subsequent reaction.

EXAMPLE 12

5-Amino-1-(4-[4-chlorobenzoyl]-3-chlorobenzyl)-1,2,3-triazole-4-carboxamide

A stirred suspension of 2-cyanoacetamide (378 mg, 4.50 mmol) in ethanol (15 ml) was treated with sodium methoxide (236 mg, 4.37 mmol), refluxed 10 minutes, cooled slightly, and treated with 4-(4-chlorobenzoyl)-3-chlorobenzyl azide (1.03 g, 3.36 mmol) dissolved in ethanol (4 ml). The mixture was refluxed 2 hours, cooled to ambient temperature, and filtered. The solids were washed with ethanol, and the combined filtrate and wash were evaporated to dryness under vacuum. The residue was dissolved in 19:1 (v/v) dichloromethane-methanol (40 ml) and chromatographed on a column of silica gel (60 g) eluted in 20 ml fractions with 97:3 (v/v) dichloromethane-methanol. Fractions 15–42 were combined and evaporated under vacuum to provide 402 mg (32%) of 5-amino-1-(4-[4-chlorobenzoyl]-3-chlorobenzyl)-1,2,3-triazole-4-carboxamide, m.p. 203°–205° C.

EXAMPLE 13

3-(4-Chlorobenzoyl)-4-chlorotoluene

A stirred solution of 2-chloro-5-methylbenzoyl chloride (9.41 g, 49.8 mmol) in chlorobenzene (14 ml) at 80° C. was treated with aluminum chloride (7.32 g, 54.9 mmol) in portions over 15 minutes. The mixture was stirred 15 hours at 80° C., cooled, quenched by addition of ice and concentrated hydrochloric acid (5.0 ml) and extracted with diethyl ether (2×50 ml). The combined extracts were washed with water, dried over anhydrous magnesium sulfate, and evaporated under vacuum. The residue was crystallized from n-hexane to provide 10.4 g (79%) of 3-(4-chlorobenzoyl)-4-chlorotoluene, m.p. 85°–90° C. Recrystallization raised the melting point to 90°–92° C.

EXAMPLE 14

3-(4-Chlorobenzoyl)-4-chlorobenzyl bromide

A refluxing solution of 3-(4-chlorobenzoyl)-4-chlorotoluene (5.3 g, 20. mmol) and dibenzoylperoxide (200 mg, 0.83 mmol) in benzene (200 ml) was treated in portions with N-bromosuccinimide (4.4 g, 25. mmol) over 20 minutes. The mixture was refluxed 15 hours, cooled and filtered. The filtrate was evaporated under vacuum, triturated with diethyl ether (150 ml), filtered, and evaporated under vacuum. The residue was chromatographed on silica gel (500 g) eluted with 97:3 (v/v) n-hexane-ethyl acetate using a preparative high-performance liquid chromatograph to provide 3.47 g (50%) of 3-(4-chlorobenzoyl)-4-chlorobenzyl bromide, m.p. 81°–83° C.

EXAMPLE 15

3-(4-Chlorobenzoyl)-4-chlorobenzyl azide

A suspension of 3-(4-chlorobenzoyl)-4-chlorobenzyl bromide (2.67 g, 7.76 mmol) and sodium azide (1.25 g, 19.2 mmol) in ethanol (25 ml) was stirred 5 hours at reflux and 16 hours at ambient temperature. The mixture was filtered and the solids washed with ethanol. The combined filtrate and wash were evaporated under vacuum and the residue was treated with diethyl ether (50 ml) and filtered. The filtrate was evaporated to dryness under vacuum to provide 2.21 g (93%) of oily 3-(4-chlorobenzoyl)-chlorobenzyl azide, IR (neat): 2100, 1670 cm$^{-1}$.

EXAMPLE 16

5-Amino-1-(3-[4-chlorobenzoyl]-4-chlorobenzyl)-1,2,3-triazole-4-carboxamide

To a stirred solution of sodium (0.147 g, 6.41 mmol) in ethanol (20 ml) under nitrogen atmosphere was added 2-cyanoacetamide (539 mg, 6.41 mmol) and the mixture was refluxed 10 minutes. The mixture was cooled slightly, 3-(4-chlorobenzoyl)-4-chlorobenzyl azide (1.51 g, 4.93 mmol) was added, and the mixture was refluxed 1 hour. The mixture was cooled to 0° C. and filtered. The product was washed with ice cold ethanol (2×5 ml), water (3×5 ml), ice cold ethanol (2×5 ml), and diethyl ether (10 ml), and dried at 50° C. for 3 hours under vacuum to provide 1.16 g (60%) of 5-amino-1-(3-[4-chlorobenzoyl]-4-chlorobenzyl)-1,2,3-triazole-4-carboxamide, m.p. 189°–192° C.

EXAMPLE 17

2,6-Dichloro-4-methylacetanilide

Gaseous chlorine was bubbled into a stirred suspension of acetanilide (64.2 g, 430 mmol) and anhydrous ferric chloride (1.5 g, 9.2 mmol) in glacial acetic acid (240 ml). The internal temperature spontaneously rose to 60° C. and was maintained at 60°±5° C. by intermittent warming for 2 hours. Excess chlorine was removed with a stream of nitrogen for 30 minutes, the mixture was cooled, slowly poured into ice-water (1 L), and filtered. The crude product was washed with water (3X), dissolved in dichloromethane (2 L), washed with saturated aqueous sodium bicarbonate and water, and dried over anhydrous magnesium sulfate. The solvent was evaporated under vacuum and the residue was triturated with ether (100 ml), filtered, and washed with diethyl ether (100 ml). Drying and crystallizing from absolute ethanol (230 ml) afforded 24.9 g (27%) of 2,6-dichloro-4-methylacetanilide, m.p. 196°–199° C. Recrystallization from ethanol provided material m.p. 201.5°–204° C.

EXAMPLE 18

2,6-Dichloro-4-methylaniline

A vigorously stirred suspension of 2,6-dichloro-4-methylacetanilide (67.0 g, 307 mmol) in 6N hydrochloric acid (1.1 L) was refluxed 2.25 hours, cooled, kept 16 hours at ambient temperature, and slowly basified to pH 10 with 50% (w/v) aqueous sodium hydroxide (290 ml). The mixture was extracted twice with dichloromethane and the combined extracts were washed with water, dried over anhydrous magnesium sulfate, and evaporated under vacuum to provide 49.8 g (92%) of 2,6-dichloro-4-methylaniline, m.p. 50°–52° C.

EXAMPLE 19

2,6-Dichloro-4-methylbenzonitrile

Powdered sodium nitrite (20.8 g, 650 mmol) was added in portions to stirred concentrated sulfuric acid (146 ml) at 5° C. The mixture was stirred 30 minutes at ambient temperature and 30 minutes at 50° C., cooled to 5° C., and treated dropwise with a solution of 2,6-dichloro-4-methylaniline (47.0 g, 267 mmol) in acetic acid (158 ml). The mixture was stirred 3 hours at 15° C., slowly poured into a solution of sodium carbonate (253 g, 2.39 mole), potassium cyanide (93.5 g, 1.44 mole), and nickel (III) chloride hexahydrate (45.4 g, 166 mmol) in water (1.3 L). After gas evolution subsided the mixture was stirred for 1 hour at 35° C., cooled, and extracted with diethyl ether. The combined extracts were washed with water, dried over anhydrous magnesium sulfate, and evaporated under vacuum. The residue was dissolved in dichloromethane and chromatographed on a column of silica gel (300 g) eluted with dichloromethane. After a forerun (600 ml), 1 liter of eluent was collected and evaporated under vacuum. The residue was crystallized from n-hexane (200 ml) to provide 14.8 g 2,6-dichloro-4-methylbenzonitrile. The mother liquor was diluted with diethyl ether and chromatographed on silica gel (500 g) using a preparative high-performance liquid chromatograph to provide 7.3 g of product (total yield: 22.1 g [44%]), m.p. 99°–102° C.

EXAMPLE 20

2,6-Dichloro-4-methylbenzamide

To stirred, cooled concentrated sulfuric acid (40 ml) was added in portions 2,6-dichloro-4-methylbenzonitrile (13.2 g, 71.0 mmol). The mixture was heated on a steam bath for 3 hours with occasional shaking, cooled, poured into ice-water, and extracted twice with dichloromethane. The combined extracts were washed with brine, dried over anhydrous magnesium sulfate, and evaporated under vacuum. The residue was chromatographed on a column of silica gel (390 g) eluted with 4:1 (v/v) dichloromethane-diethyl ether to provide 8.6 g (59%) of 2,6-dichloro-4-methylbenzamide, m.p. 101°–107° C.

EXAMPLE 21

2,6-Dichloro-4-methylbenzoic acid

A stirred 0° C. solution of 2,6-dichloro-4-methylbenzamide (8.6 g, 42. mmol) in 2:1 (v/v) acetic acid-concentrated hydrochloric acid (165 ml) was treated dropwise with a solution of sodium nitrite (19.0 g, 275 mmol) in water (42 ml). The mixture was stirred 30 minutes at 5° C., slowly warmed to 85° C., and kept 1 hour. The mixture was cooled, concentrated under vacuum, and treated with cold water (50 ml). The product was filtered, washed twice with cold water, and dried 16 hours at 50° C. over phosphorus pentoxide under vacuum to provide 7.15 g (83%) of 2,6-dichloro-4-methylbenzoic acid, m.p. 139°–145° C.

EXAMPLE 22

1-(2,6-Dichloro-4-methylphenyl)-1-(4-chlorophenyl)-methyleneimine hydrochloride A stirred mixture of 4-chloroiodobenzene (1.30 g, 5.45 mmol) and magnesium turnings (118 mg, 4.85 mmol) in dry diethyl ether (5.0 mL) was refluxed 1.5 hours under nitrogen atmosphere. A solution of 2,6-dichloro-4-methylbenzonitrile (844 mg, 4.54 mmol) in dry toluene (10 mL) was added, diethyl ether was distilled off, and the resulting solution was refluxed 1.5 hours. The mixture was cooled to −10° C., quenched by addition of water (20 mL) and concentrated aqueous ammonia (15 mL), diluted with toluene (15 mL), and filtered. The filtrate was separated and the aqueous phase extracted with diethyl ether (3×5 mL). The combined organic phases were dried over anhydrous magnesium sulfate, treated with activated charcoal, filtered, and evaporated under vacuum. The residual glass was dissolved in diethyl ether (40 mL), cooled to 0° C., and stirred while hydrogen chloride was slowly bubbled into the solution. The precipitate was collected by filtration, washed with diethyl ether, and dried for 3 hours at 50° C. under vacuum to provide 855 mg (56%) 1-(2,6-dichloro-4-methylphenyl)-1-(4-chlorophenyl)methyleneimine hydrochloride, m.p. 215°–220° C. (dec).

EXAMPLE 23

4-(t-Butyldimethylsilyloxymethyl)-2,4',6-trichlorobenzophenone

A stirred -55° C. solution of 3,5-dichlorobenzyl t-butyldimethylsilyl ether (1.46 g, 5.00 mmol) and tetramethylethylenediamine (0.755 mL, 0.581 g, 5.01 mmol) in tetrahydrofuran (5 mL) under nitrogen atmosphere was treated dropwise over 10 minutes with a 1.6 M solution of n-butyllithium in hexane (3.3 mL, 5.25 mmol). After 30 minutes at −55° C., a solution of p-chlorobenzoyl chloride (0.875 g, 5.00 mmol) in tetrahydrofuran (1.0 mL) was added over 15 minutes. The resulting mixture was stirred 2 hours at −55° to −30° C. and 1.5 hours at ambient temperature. The reaction was quenched by addition of saturated aqueous ammonium chloride (1.1 mL) and stirred 30 minutes. The mixture was treated with sodium sulfate (1.1 g), stirred 1 hour, and decanted. The residual solid was washed well with diethyl ether. The combined solution and washes were extracted twice with water, once with 10% aqueous citric acid, and once with brine, dried over anhydrous magnesium sulfate, and evaporated under vacuum to provide 1.93 g of crude brown oil. A total of 585 mg of oil was chromatographed on eight 1000μ 20 cm×20 cm silica gel preparative thick layer chromatography plates developed with 5:1 (v/v) hexane-ethyl acetate to provide 356 mg (60%) 4-(t-butyldimethylsilyloxymethyl)-2,4',6-trichlorobenzophenone; NMR (CDCl$_3$): 0.14 s (6H), 0.95 s (9H), 4.72 s (2H), 7.27 s (2H), 7.35 d (J=9Hz, 2H), 7.70 d (J=9Hz, 2H).

EXAMPLE 24

4-(4-Chlorobenzoyl)-3,5-dichlorotoluene

Method A:

A solution of 2,6-dichloro-4methylbenzoic acid (7.15 g, 34.9 mmol) in thionyl chloride (133 ml) containing dimethylformamide (1.3 ml) was refluxed 3 hours, evaporated under vacuum, and azeotroped twice with benzene. The residue was triturated with petroleum ether (b.p. 30°–60° C., 200 ml) and filtered. The filtrate was evaporated under vacuum to provide 8.5 g (109% of theory) 2,6-dichloro-4-methylbenzoyl chloride, IR (neat): 1785 cm$^{-1}$. The crude chloride and chlorobenzene (94 g) were stirred in carbon tetrachloride (235 ml), treated in portions with aluminum chloride (5.35 g, 40.1 mmol), kept 30 minutes at ambient temperature, and refluxed 3 hours. The mixture was cooled, quenched by addition of ice and concentrated hydrochloric acid, and extracted three times with dichloromethane. The combined extracts were washed with water, dried over anhydrous magnesium sulfate, and evaporated under vacuum. The residue was chromatographed on a column of silica gel (400 g) eluted with 3:2 (v/v) dichloromethane-hexane to provide 7.19 g (69%) of 4-(4-chlorobenzoyl)-3,5-dichlorotoluene, m.p. 111.5°–114° C.

Method B:

A stirred solution of 1-(2,6-dichloro-4-methyl)-2-(4-chlorophenyl)methyleneimine hydrochloride (100 mg, 0.300 mmol) in 2:1 (v/v) dioxane-aqueous phosphate buffer (pH 7) (6.0 mL) was refluxed 48 hours, cooled, diluted with water (10 mL), and extracted with diethyl ether (3×7 mL). The combined extracts were washed with brine (10 mL), dried over anhydrous magnesium sulfate, and evaporated under vacuum. The residue was chromatographed on one 20 cm×20 cm 1000μ silica gel preparative thick layer chromatography plate developed with 3:2 (v/v) hexane-dichloromethane to provide 37 mg (41%) 4-(4-chlorobenzoyl)-3,5-dichlorotoluene.

Method C:

A stirred, −60° C. solution of 3,5-dichlorotoluene (805 mg, 5.00 mmol) in tetrahydrofuran (5 mL) under nitrogen atmosphere was treated dropwise over 10 minutes with a 1.6M solution of n-butyllithium in hexane (3.3 mL, 5.25 mmol). After addition was complete residual n-butyllithium in the addition funnel was rinsed into the reaction mixture with tetrahydrofuran (1 mL). The reaction mixture was stirred 30 minutes at −55° and then a solution of p-chlorobenzoylchloride (875 mg, 5.00 mmol) in tetrahydrofuran (1.0 mL) was added dropwise over 15 minutes. The mixture was kept at −55° to −30° C. for 2 hours, stirred 2 hours at ambient temperature, and quenched by addition of saturated aqueous ammonium chloride (1.1 mL). After stirring 15 minutes, sodium sulfate (1.1 g) was added, and the mixture was stirred an additional 15 minutes. The solution was decanted, the solids were washed with diethyl ether, and the combined solution and wash were evaporated under reduced pressure. The residue was recrystallized from ethanol (15 mL) to provide 0.78 g (52%) 4-(4-chlorobenzoyl)-3,5-dichlorotoluene.

EXAMPLE 25

4-(4-Chlorobenzoyl)-3,5-dichlorobenzyl bromide

Method A:

A refluxing solution of 4-(4-chlorobenzoyl)-3,5-dichlorotoluene (7.19 g, 24.0 mmol) and dibenzoylperoxide (370 mg, 1.53 mmol) in benzene (247 ml) was treated in portions with N-bromosuccinimide (7.53 g, 42.3 mmol). The mixture was refluxed 24 hours, cooled, and filtered. The precipitate was washed once with benzene, and the combined filtrate and washings were evaporated under vacuum. The residue was triturated with diethyl ether and filtered, and the filtrate was evaporated under vacuum. The residue was chromatographed on silica gel (500 g) eluted with 7:3 (v/v) n-hexanedichloromethane using a preparative high-performance liquid chromatograph to provide 3.2 g (35%) of 4-(4-chlorobenzoyl)-3,5-dichlorobenzyl bromide, m.p. 69°–73° C.

Method B:

A solution of 4-(t-butyldimethylsilyloxymethyl)-2,4′,6-trichlorobenzophenone (356 mg, 0.839 mmol) in acetic acid (6 mL), tetrahydrofuran (3 mL), and water (2 mL) was stirred for 44 hours at ambient temperature, 7 hours at 80° C., and 12 hours at ambient temperature. The mixture was diluted with diethyl ether (25 mL), washed with water (4×), saturated aqueous sodium bicarbonate (3×), and brine, dried over anhydrous magnesium sulfate, and evaporated under vacuum. The residue was dissolved in diethyl ether (3 mL), stirred at 0° C., and treated with phosphorus tribromide (3.1 mL). The mixture was stirred 1 hour at 0° C. and 24 hours at ambient temperature. The reaction was quenched by addition of ice chips (5 g), diluted with diethyl ether (20 mL), and separated. The organic phase was washed with water, saturated aqueous sodium bicarbonate (2×), and brine, dried over anhydrous magnesium sulfate, and evaporated under vacuum to provide 240 mg (77%) solid 4-(4-chlorobenzoyl)-3,5-dichlorobenzyl bromide.

EXAMPLE 26

4-(4-Chlorobenzoyl)-3,5-dichlorobenzyl azide

A suspension of 4-(4-chlorobenzoyl)-3,5-dichlorobenzyl bromide (3.2 g, 8.5 mmol) and potassium azide (1.3 g, 16 mmol) in ethanol (32 ml) was refluxed 5 hours, cooled, and filtered. The precipitate was washed once with ethanol and the combined filtrate and wash were evaporated under vacuum. The residue was triturated with diethyl ether (50 ml) and filtered. The filtrate was evaporated under vacuum to provide 2.92 g (100%) of 4-(4-chlorobenzoyl)-3,5-dichlorobenzyl azide, m.p. 50°–55° C.

EXAMPLE 27

5-Amino-1-(4-[4-chlorobenzoyl]-3,5-dichlorobenzyl)-1,2,3-triazole-4-carboxamide

Method A:

A suspension of 2-cyanoacetamide (149 mg, 1.77 mmol) in ethanol (5 ml) was refluxed 20 minutes with sodium methoxide (93 mg, 1.72 mmol), cooled slightly, treated with 4-(4-chlorobenzoyl)-3,5-dichlorobenzyl azide (450 mg, 1.32 mmol), and refluxed 1 hour. The mixture was cooled, evaporated under vacuum, and chromatographed on a column of silica gel (50 g), eluted with 19:1 (v/v) dichloromethane-methanol to provide 231 mg (41%) of 5-amino-1(4-[4-chlorobenzoyl]-3,5-dichlorobenzyl)-1,2,3-triazole-4-carboxamide, m.p. 198.5°–200° C.

Method B:

A stirred ambient temperature solution of 5-amino-1,2,3-triazole-4-carboxamide (630 mg, 4.96 mmol) in dry dimethylformamide (20 ml) was treated in one portion with sodium hydride (230 mg of a 50% suspension in mineral oil, 115 mg NaH, 4.79 mmol). After 15 min. solid 4-(4-chlorobenzoyl)-3,5-dichlorobenzyl bromide was added in one portion. The mixture was stirred 1 hour, poured into water (20 ml), acidified to pH 6 with glacial acetic acid, and filtered. The solid was washed three times with water and dissolved in dichloromethane. The layers were separated and the organic phase was dried over anhydrous magnesium sulfate and evaporated under vacuum. The residue was chromatographed on a column of silica gel (200 g) eluted with 97:3 (v/v) dichloromethane-methanol to provide 351 mg (17%) 5-amino-1-(4-[4-chlorobenzoyl]-3,5-dichlorobenzyl)-1,2,3-triazole-4-carboxamide.

EXAMPLE 28

3-Chloro-4-(4-chlorophenylthio)benzamide

To a solution of 3,4-dichlorobenzamide (95.0 g, 0.500 mole) in dry dimethylformamide (1 liter) was added in one portion potassium 4-chlorothiophenolate (118.8 g, 0.650 mole). The mixture was stirred under nitrogen at 100° C. for 8 hours and at ambient temperature for 16 hours. Solvent (750 ml) was removed by vacuum distillation at 45° C. and the residue was poured into ice water (3 liters) containing concentrated hydrochloric acid (25 ml). The precipitate was filtered, partially dried, and crystallized from hot ethanol (1.2 liters). The crystals were filtered, washed with ethanol, and dried at 45° C. for 18 hours under vacuum to provide 102.0 g (68%) of 3-chloro-4-(4-chlorophenylthio)benzamide, m.p. 176°–177° C.

EXAMPLE 29

3-Chloro-4-(4-chlorophenylthio)benzylamine

A solution of 3-chloro-4-(4-chlorophenylthio)benzamide (44.7 g, 150 mmol) in tetrahydrofuran (300 ml) was added dropwise over 30 minutes to a stirred 1.0M solution of borane in tetrahydrofuran (450 ml) under a nitrogen atmosphere at ambient temperature. The mixture was refluxed for 16 hours, cooled to 0° C., and quenched by addition of 2.0N hydrochloric acid. The solvent was evaporated under vacuum and the solid residue was slurried in water, filtered, and washed with water (4×300 ml). The solid was partially dried in the air, washed with diethyl ether (3×200 ml), and dried under vacuum at 50° C. for 3 hours and at ambient temperature for 16 hours. The crude product was suspended in diethyl ether (700 ml), vigorously stirred for 30 minutes, filtered, washed with diethyl ether, and dried to provide 27.5 g (57%) 3-chloro-4-(4-chlorophenylthio) benzylamine hydrochloride, m.p. 237°–240° C. The free base was liberated by slurrying the salt (6.77 g) in water (100 ml), basifying with 2.5N aqueous sodium hydroxide, adding diethyl ether (100 ml), and filtering. The biphasic filtrate was separated and the aqueous phase was extracted with diethyl ether. The combined diethyl ether phases were washed with water and brine, dried over anhydrous magnesium sulfate, and evaporated under vacuum. The oily residue was kept under vacuum at ambient temperature for 16 hours to provide 5.80 g (97%) of 3-chloro-4-(4-chlorophenylthio)benzylamine as a colorless oil, 60 MHz $^1$H NMR (DMSO-$d_6$): 2.22 broad s (2H), 3.37 s (2H), 7.1–7.5 complex m (7H); (DMSO-$d_6$/$D_2O$/DCl) 4.05 s (2H), 7.03 d (J=9Hz, 1H), 7.3–7.6 broad m (6H).

EXAMPLE 30

3-Chloro-4-(4-chlorophenylthio)benzyl azide

A solution of 3-chloro-4-(4-chlorophenylthio)benzylamine (5.80 g, 20.4 mmol) in absolute ethanol (55 ml) was stirred at ambient temperature and treated in one portion with 2,4,6-triphenylpyrylium tetrafluoroborate (6.4 g, 16.4 mmol). After stirring 1 hour a red gum had separated and the mixture was made homogeneous by adding dimethylformamide (55 ml). The mixture was stirred 16 hours and evaporated to dryness at 60° C. under vacuum. The residual red gum was dissolved in dimethylformamide (40 ml), stirred at ambient temperature, and treated in one portion with dry sodium azide (4.0 g, 62 mmol). The mixture was heated to 130° C. for 6 hours, kept 16 hours at ambient temperature, diluted with water (200 ml), and extracted with diethyl ether (3×100 ml). The combined extracts were washed with water (2×150 ml) and brine (150 ml), dried over anhydrous magnesium sulfate, and evaporated under vacuum to provide 10.0 g reddish semi-solid. The crude product was chromatographed on a column of silica gel (1.2 liters) eluted in 50 ml fractions with 2:1 (v/v) hexane-methylene chloride. Appropriate fractions were pooled and evaporated under vacuum to provide 1.9 g (37%) of 3-chloro-4-(4-chlorophenylthio)benzyl azide, m.p. 39°–41° C.

EXAMPLE 31
5-Amino-1-(3-chloro-4-[4-chlorophenylthio]benzyl)-1,2,3-triazole-4-carboxamide To a stirred solution of sodium (276 mg, 12.0 mmol) in absolute ethanol (28 ml) at 60° C. was added 2-cyanoacetamide (952 mg, 11.3 mmol). The mixture was stirred 5 minutes, 3-chloro-4-(4-chlorophenylthio)benzyl azide (1.8 g, 5.8 mmol) was added, and the mixture was refluxed for 1 hour. The mixture was cooled to 0° C. and filtered. The solid product was washed with ethanol (2X), water (4X), ethanol (2X), and diethyl ether, and air dried to provide 1.67 g (73%) of 5-amino-1-(3-chloro-4-[4-chlorophenylthio]-benzyl)-1,2,3-triazole-4-carboxamide, m.p. 202°–203.5° C.

EXAMPLE 32
5-Amino-1-(3-chloro-4-[4-chlorophenylsulfinyl]benzyl-1,2,3-triazole-4-carboxamide A stirred suspension of 5-amino-1-(3-chloro4-[4-chlorophenylthio]benzyl)-1,2,3-triazole-4-carboxamide (475 mg, 1.20 mmol) in methanol (160 ml) was treated with trifluoroacetic acid (278 μl, 411 mg, 3.61 mmol), warmed until homogeneous, and cooled to ambient temperature. To this solution was added m-chloroperbenzoic acid (244 mg of 85% technical grade, 1.20 mmol), the mixture was stirred 75 minutes, an additional portion of m-chloroperbenzoic acid (33.1 mg of 85% technical grade, 0.163 mmol) was added, and the mixture was stirred an additional 45 minutes. The mixture was treated with 2.5N aqueous sodium hydroxide (2.5 ml), stirred until crystallization commenced, concentrated to approximately 40 ml under vacuum at 30° C., and chilled to 0° C. The precipitate was filtered, washed with methanol, and dried to afford 410 mg (83%) of 5-amino-1-(3-chloro-4-[4-chlorophenylsulfinyl]benzyl)-1,2,3-triazole-4-carboxamide, m.p. 237°–238° C.

EXAMPLE 33
5-Amino-1-(3-chloro-4-[4-chlorophenylsulfonyl]benzyl-1,2,3-triazole-4-carboxamide A stirred suspension of 5-amino-1-(3-chloro-4-[4-chlorophenylthio]benzyl)-1,2,3-triazole-4-carboxamide (475 mg, 1.20 mmol) in methanol (160 ml) was treated with trifluoroacetic acid (278 μl, 411 mg, 3.61 mmol), warmed until homogeneous, and cooled to ambient temperature. To this solution was added m-chloroperbenzoic acid (582 mg of 85% technical grade, 2.86 mmol), the mixture was stirred 19.5 hours at ambient temperature, an additional portion of m-chloroperbenzoic acid (610 mg of 85% technical grade, 3.00 mmol) was added, and the mixture was stirred at 50° C. for 15 hours. The mixture was cooled to 0° C. and filtered. The product was washed with methanol and dried to provide 240 mg of 5-amino-1-(3-chloro-4-[4-chlorophenylsulfonylbenzyl)-1,2,3-triazole-4-carboxamide, m.p. 239°–241° C. The filtrate was concentrated at 30° C. under vacuum to provide an additional 60 mg of product. Total yield was 300 mg (58%).

EXAMPLE 34
4-(4-Chlorophenylthio)-3,5-dichlorobenzamide

A solution of 3,4,5-trichlorobenzamide (25.0 g, 111 mmol) and potassium 4-chlorothiophenolate (29.0 g, 159 mmol) in dimethylformamide (220 ml) was stirred for 3 days at ambient temperature under nitrogen atmosphere, poured into ice water (2.2 L), and filtered. The solid was washed with water, partially dried under vacuum, suspended in diethyl ether (200 ml), filtered, and washed with diethyl ether (2×75 ml). The residue was triturated with diethyl ether (75 ml), filtered, again triturated with diethyl ether (75 ml), filtered, and dried under vacuum to provide 21.2 g (57%) of 4-(4-chlorophenylthio)-3,5-dichlorobenzamide, m.p. 171°–174° C.

EXAMPLE 35
4-(4-Chlorophenylthio)-3,5-dichlorobenzylamine

A solution of 4-(4-chlorophenylthio)-3,5-dichlorobenzamide (25.7 g, 77.3 mmol) in tetrahydrofuran (155 ml) was added dropwise over 25 minutes to a stirred 1.0M solution of borane in tetrahydrofuran (232 ml) at ambient temperature under nitrogen atmosphere. The mixture was refluxed for 16 hours, cooled to 0° C., and quenched by addition of 2.0N hydrochloric acid. Solvent was evaporated under vacuum and the residue treated with water (400 ml) and diethyl ether. The mixture was basified with 2.5N aqueous sodium hydroxide, the phases were separated, and the aqueous phase extracted twice with diethyl ether. The combined extracts were washed with water (2X) and brine, dried over anhydrous magnesium sulfate, and evaporated under vacuum. The residual oil was dissolved in methanol (500 ml), treated with concentrated hydrochloric acid, and evaporated to dryness at 50° C. under vacuum. The residue was azeotroped twice with methanol, stirred 30 minutes with diethyl ether (300.ml), filtered, washed with diethyl ether (4X), and dried at 40° C. under vacuum to provide 22.3 g (81%) of 4-(4-chlorophenylthio)-3,5-dichlorobenzylamine hydrochloride, m.p. 217°–219° C. The free base was liberated by suspending the salt (4.0 g) in water, basifying with dilute aqueous sodium hydroxide, and extracting with diethyl ether (3X). The combined extracts were washed with water (2X) and brine, dried over anhydrous magnesium sulfate, and evaporated under vacuum to provide 3.59 g (100%) of oily free base.

EXAMPLE 36
4-(4-Chlorophenylthio)-3,5-dichlorobenzoic acid and 4-(4-Chlorophenylsulfinyl)-3,5-dichlorobenzoic acid A solution of 4-(4-chlorophenylthio)-3,5-dichlorobenzamide (5.00 g, 15.0 mmol) in glacial acetic acid (500 ml) containing concentrated hydrochloric acid (100 ml) was stirred at ambient temperature while a solution of sodium nitrite (6.90 g, 10.0 mmol) in water (50 ml) was added dropwise over 10 minutes. The mixture was stirred 1 hour at ambient temperature, warmed to 80° C. over 50 minutes, kept at 80°–85° C. for 1 hour, and cooled to ambient temperature over 2 hours. The mixture was concentrated under vacuum, the residue was diluted with water (800 ml), and filtered. The product was washed well with water and dried at 50° C. under vacuum to provide 4.91 g of a 2:3 mixture of 4-(4-chlorophenylthio)-3,5-dichlorobenzoic acid (A) and 4-(4-chlorophenylsulfinyl)-3,5-dichlorobenzoic acid (B). 60 MHz $^1$H NMR (DMSO-$d_6$) A: 7.66 s (4H), 7.94 s (2H); B: 7.10 dm (J=8.5 Hz, 2H), 7.37 dm (J=8.5 Hz, 2H), 8.03 s (2H).

EXAMPLE 37

4-(4-Chlorophenylthio)-3,5-dichlorobenzyl alcohol and 4-(4-Chlorophenylsulfinyl)-3,5-dichlorobenzyl alcohol A 0° C. stirred solution of a 2:3 mixture of 4-(4-chlorophenylthio)-3,5-dichlorobenzoic acid and 4-(4-chlorophenylsulfinyl)-3,5-dichlorobenzoic acid (4.18 g) in tetrahydrofuran (125 ml) under nitrogen atmosphere was treated dropwise over 25 minutes with a 1.0M solution of borane in tetrahydrofuran (35 ml). After vigorous gas evolution ceased the mixture was stirred 18 hours at ambient temperature, cooled to 0° C., and quenched by addition of water. The mixture was diluted with ice water (600 ml) containing 2.0N hydrochloric acid (15 ml) and extracted with diethyl ether (3×250 ml). The combined extracts were washed with water (2X) and brine, dried over anhydrous magnesium sulfate, and evaporated under vacuum. The solid residue was stirred with diethyl ether (45 ml) for 1 hour at ambient temperature, filtered, and washed with diethyl ether (3X). The solid was again stirred with diethyl ether (20 ml) for 30 minutes, filtered, washed with diethyl ether, and air dried to provide 1.88 g solid 4-(4-chlorophenylsulfinyl)-3,5-dichlorobenzyl alcohol (A). All the aforementioned filtrates were combined, evaporated, and chromatographed on a column of silica gel eluted in 18 ml fractions with 49:1 (v/v) dichloromethanemethanol. Fractions 22–37 were combined and evaporated under vacuum to provide 1.28 g of solid 4-(4-chlorophenylthio)-3,5-dichlorobenzyl alcohol (B). Fractions 38–60 were combined, evaporated under vacuum, and the residue was triturated with diethyl ether, filtered, washed with diethyl ether, and dried under vacuum to provide 486 mg of A (total yield: 2.37 g); 60 MHz $^1$H NMR (DMSO-$d_6$) A: 4.56 d (J=5 Hz, 2H), 5.56 t (J=5 Hz, 1H), 7.50 s (2H), 7.60 s (4H); B: 4.56 d (J=6 Hz, 2H), 5.53 t (J=6 Hz, 1H), 7.01 dm (J=8.5 Hz, 2H), 7.34 dm (J=8.5 Hz, 2H), 7.57 s (2H).

EXAMPLE 38

4-(4-Chlorophenylthio)-3,5-dichlorobenzyl azide

Method A:

A stirred solution of 4-(4-chlorophenylthio)-3,5-dichlorobenzylamine (3.59 g, 11.3 mmol) in absolute ethanol (30 ml) at ambient temperature was treated in one portion with 2,4,6-triphenylpyrylium tetrafluoroborate (3.58 g, 9.06 mmol). The mixture was stirred 30 minutes, diluted with dimethylformamide (30 ml), and stirred 16 hours. The solvent was evaporated under vacuum at 60° C. and the residue was triturated with diethyl ether (2×25 ml). The residual solid was dissolved in dry dimethylformamide (23 ml), dry sodium azide (2.27 g, 34.9 mmol) was added, and the mixture was stirred at 130° C. for 6 hours and ambient temperature for 4 days. The mixture was diluted with water (250 ml) and extracted twice with diethyl ether. The combined extracts were washed with water (2X) and brine, dried over anhydrous magnesium sulfate, and evaporated under vacuum. The residue was disolved in dichloromethane, silica gel (60 g) was added, and the mixture was dried under vacuum, placed on a column of silica gel (600 ml), and eluted in 50 ml fractions with 1:2 (v/v) dichloromethane-hexane. After a forerun, fractions 8–14 were combined and evaporated under vacuum to provide 320 mg oily 4-(4-chlorophenylthio)-3,5-dichlorobenzyl azide. Fractions 15–22 were combined, evaporated under vacuum, and the residue was chromatographed on one 20 cm×20 cm 1500$\mu$ silica gel preparative thick layer chromatography plate developed with 1:2 (v/v) dichloromethanehexane. Product was eluted with dichloromethane and solvent was evaporated under vacuum to provide an additional 62 mg of oily azide (total yield: 382 mg [10%]).

Method B:

4-(4-Chlorophenylthio)-3,5-dichlorobenzyl alcohol (1.28 g, 4.00 mmol) was added to stirred thionyl chloride (5.0 ml) at ambient temperature. The solution was refluxed 15 minutes, treated with dimethylformamide (1 drop), refluxed 15 minutes, treated with more dimethylformamide (1 drop), and refluxed 1 hour. Thionyl chloride was evaporated under a stream of nitrogen, hexane (5 ml) was added and evaporated under a stream of nitrogen, and the residue was dried under vacuum. Hexane (10 ml) was added, the mixture was filtered through anhydrous magnesium sulfate, and the magnesium sulfate was washed well with hexane. The combined filtrate and washes were evaporated under vacuum and dried at 35° C. under vacuum to provide 1.35 g (100%) of 4-(4-chlorophenylthio)-3,5-dichlorobenzyl chloride. The chloride was suspended in absolute ethanol (10 ml) and stirred at ambient temperature while sodium azide (720 mg, 11.1 mmol) was added. The mixture was refluxed 3 hours, kept 16 hours at −20° C., and evaporated to dryness under vacuum at 30° C. The residue was treated with diethyl ether (50 ml), filtered, and washed with diethyl ether. The combined filtrate and washes were evaporated under vacuum and dried to provide 1.38 g (100%) of 4-(4-chlorophenylthio)-3,5-dichlorobenzyl azide as a colorless viscous oil; 60 MHz $^1$H NMR (CDCl$_3$) 4.35 s (2H), 7.03 dm (J=8.5 Hz, 2H), 7.23 dm (J=8.5 Hz, 2H), 7.38 s (2H); IR (neat): 2110 cm$^{-1}$.

EXAMPLE 39

5-Amino-1-(4-[4-chlorophenylthio]-3,5-dichlorobenzyl)1,2,3-triazole-4-carboxamide A solution of sodium (100 mg, 4.35 mmol) in absolute ethanol (10.9 ml) was stirred at 60° C., treated with 2-cyanoacetamide (365 mg, 4.34 mmol), and stirred 5 minutes. A solution of 4-(4-chlorophenylthio)-3,5-dichlorobenzyl azide (1.36 g, 3.95 mmol) in absolute ethanol (7.0 ml) was added and the mixture was refluxed 1 hour. The mixture was cooled, filtered, and washed with ethanol. The combined filtrate and washes were acidified with glacial acetic acid and concentrated to a small volume under vacuum. The residue was diluted with water (150 ml), extracted with diethyl ether (3X), and the combined extracts were washed with water, shaken with brine, filtered, and separated. The organic phase was evaporated to dryness at 30° C. under vacuum to provide 1.66 g of yellow foam. The foam was chromatographed on a column of silica gel (320 ml) eluted in 20 ml fractions with 19:1 (v/v) dichloromethane-methanol. Fractions 28–41 were combined and evaporated to dryness under vacuum. The residue was triturated with diethyl ether (10 ml), filtered, washed with diethyl ether, and dried 16 hours at ambient temperature under vacuum to provide 425 mg (25%) of 5-amino-1-(4-[4-chlorophenylthio]-3,5-dichlorobenzyl)-1,2,3-triazole-4-carboxamide, m.p. 180°–182° C.

EXAMPLE 40

5-Amino-1-(4-[4-chlorophenylsulfinyl]-3,5-dichlorobenzyl)-1,2,3-triazole

A stirred solution of 5-amino-1-(4-[4-chlorophenylthio]-3,5-dichlorobenzyl)-1,2,3-triazole-4-carboxamide (176 mg, 0.409 mmol) in glacial acetic acid (10 ml) was treated at ambient temperature with trifluoroacetic acid (94.3 μl, 139 mg, 1.23 mmol) and 30% aqueous hydrogen peroxide (2.72 ml). The mixture was stirred 45 minutes, diluted with glacial acetic acid (3.0 ml), stirred 3.25 hours, and diluted with water (100 ml). The mixture was cooled to 0° C., a small volume of diethyl ether was added, the mixture was carefully basified by addition of 50% (w/v) aqueous sodium hydroxide, and diethyl ether was evaporated under vacuum. The resulting suspension was filtered, and the solid washed well with water and dried at 45° C. under vacuum to provide 173 mg (95%) of 5-amino-1-(4-[4-chlorophenylsulfinyl]-3,5-dichlorobenzyl)-1,2,3-triazole-4-carboxamide. Recrystallization from ethanol provided material of m.p. 195°–197° C.

EXAMPLE 41

4-Benzoyl-3-methylbenzyl azide and 2-benzoyl-5-methylbenzyl azide

A stirred, ambient temperature solution of 2,4-dimethylbenzophenone (5.00 g, 23.8 mmol) in carbon tetrachloride (190 ml) was treated with N-bromosuccinimide (4.24 g, 23.8 mmol) and dibenzoylperoxide (238 mg, 0.976 mmol). The mixture was refluxed 2 hours, cooled, and evaporated to dryness of 40° C. under vacuum. The residual oil was stirred for 16 hours at ambient temperature with tetramethylguanidinium azide (5.0 g, 31.6 mmol) and evaporated under vacuum. The residual semisolid was triturated with diethyl ether, filtered, and washed with diethyl ether. The combined filtrate and washes were extracted with water (2×150 ml) and brine (200 ml), dried over anhydrous magnesium sulfate, and evaporated under vacuum. The residue was chromatographed on silica gel (500 g) eluted with 1:1 (v/v) hexane-dichloromethane using a preparative high performance liquid chromatograph to provide 942 mg of an oily 4:1 mixture of 4-benzoyl-3-methylbenzyl azide and 2-benzoyl-5-methylbenzyl azide and 731 mg of an oily mixture of these isomers. The two isomeric azides were separated by chromatography on 1000μ 20 cm×20 cm silica gel preparative thick layer chromatography plates developed three times with 1:1 (v/v) hexane-dichloromethane.

4-Benzoyl-3-methylbenzyl azide: IR (CH$_2$Cl$_2$): 2100, 1660 cm$^{-1}$; 60 MHz $^1$H NMR (CDCl$_3$) 2.35 s (3H), 4.38 s (2H), 7.2–7.9 m (8H).

2-Benzoyl-3-methylbenzyl azide: IR (CH$_2$Cl$_2$): 2100, 1660 cm$^{-1}$; 60 MHz $^1$H NMR (CDCl$_3$): 2.44 s (3H), 4.54 s (2H), 7.2–7.9 m (8H).

EXAMPLE 42

4-Amino-1-(4-benzoyl-3-methylbenzyl)-1,2,3-triazole-4-carboxamide

A stirred solution of sodium (104 mg, 4.50 mmol) in absolute ethanol at 60° C. was treated with 2-cyanoacetamide (378 mg, 4.50 mmol), kept 5 min, and treated with a solution of 942 mg of a 4:1 mixture of 4-benzoyl-3-methyl-benzyl azide and 2-benzoyl-5-methylbenzyl azide in absolute ethanol (6 ml). The mixture was refluxed 1 hour, cooled to 0°, and filtered. The solid was washed twice with water, acidified with acetic acid, and dried. The ethanol filtrate was acidified with acetic acid and evaporated to dryness at 40° C. under vacuum. The residue from the filtrate was combined with the above solid and chromatographed on a column of silica gel (125 g) eluted in 17 ml fractions with 19:1 (v/v) dichloromethane-methanol. Fractions 19–25 were combined and evaporated to dryness, and the residue was triturated with diethyl ether (3×10 ml). The remaining solid was dried 18 hours at ambient temperature under vacuum to provide 330 mg (31%) 5-amino-1-(4-benzoyl-3-methylbenzyl)-1,2,3-triazole4-carboxamide, m.p. 181°–182° C.

EXAMPLE 43

2,6-Dichloro-4-methylbenzophenone

An ambient temperature solution of 2,6-dichloro-4-methylbenzoyl chloride (5.5 g, 25 mmol) in benzene (30 ml) was treated in portions with aluminum chloride (3.45 g, 25.9 mmol). When hydrogen chloride evolution ceased, the mixture was heated at 80° C. for 15 hours. The mixture was cooled, quenched by addition of ice and concentrated hydrochloric acid (5 ml), and diluted with diethyl ether (50 ml). The layers were separated and the organic phase washed with water, dried over anhydrous magnesium sulfate, and evaporated to dryness under vacuum. The semisolid residue was chromatographed on a column of silica gel (300 g) eluted with 4:1 (v/v) hexanedichloromethane to provide 4.60 g (69%) 2,6-dichloro-4-methylbenzophenone, m.p. 75.5°–76.5° C.

EXAMPLE 44

4-Benzoyl-3,5-dichlorobenzyl bromide

A refluxing solution of 2,6-dichloro-4-methylbenzophenone (3.44 g, 13.0 mmol) and dibenzoylperoxide (325 mg, 1.34 mmol) in benzene (130 ml) was treated in portions with N-bromosuccinimide (2.75 g, 15.5 mmol). After 3 hours at reflux, the mixture was cooled and evaporated under vacuum. The residue was triturated with diethyl ether (150 ml), filtered, and evaporated under vacuum. The residue was chromatographed on a column of silica gel (250 g) eluted with 4:1 (v/v) hexane-dichloromethane to provide 2.58 g (58%) 4-benzoyl-3,5-dichlorobenzyl bromide, m.p. 111°–113° C.

EXAMPLE 45

4-Benzoyl-3,5-dichlorobenzyl azide

A mixture of 4-benzoyl-3,5-dichlorobenzyl bromide (2.37 g, 6.89 mmol) and sodium azide (1.32 g, 20:3 mmol) in absolute ethanol (31 ml) was refluxed 5 hours, cooled, and evaporated. The residue was dissolved in diethyl ether and filtered. The filtrate was evaporated to provide 1.95 g (92%) 4-benzoyl-3,5-dichorobenzyl azide, IR (neat): 2090, 1670 cm$^{-1}$.

EXAMPLE 46

5-Amino-1-(4-benzoyl-3,5-dichlorobenzyl)-1,2,3-triazole-4-carboxamide

A mixture of 2-cyanoacetamide (1.11 g, 13.2 mmol) and sodium hydroxide (544 mg, 13.6 mmol) in methanol (30 ml) was heated at 60° C. for 15 minutes, cooled slightly, and treated with a solution of 4-benzoyl-3,5-dichlorobenzyl azide (1.0 g, 3.3 mmol) in methanol (5 ml). The mixture was refluxed 5 hours, evaporated under vacuum, and chromatographed on a column of silica gel (90 g) eluted with 19:1 (v/v) dichloromethane-methanol to provide 449 mg (35%) 5-amino-1-(4-chlorobenzoyl-3,5-dichlorobenzyl)-1,2,3-triazole-4-carboxamide, m.p. 207°–210° C.

EXAMPLE 47

4-(2,6-Dichlorobenzoyl)toluene

An 80° C., stirred solution of 2,6-dichlorobenzoyl chloride (17.3 g, 82.6 mmol) in toluene (30 ml) was treated in portions with aluminum chloride (11.0 g, 82.3 mmol). After 12 hours at 80° C., the mixture was cooled, quenched with ice water and concentrated hydrochloric acid (10 ml), and separated. The aqueous phase was extracted with diethyl ether (2×150 ml) and the combined organic phases were washed twice with water, dried over anhydrous magnesium sulfate, and evaporated to dryness under vacuum. The residue was crystallized from hexane to provide 12.6 g (58%) 4-(2,6-dichlorobenzoyl)toluene, m.p. 109°–111.5° C.

EXAMPLE 48

4-(2,6-Dichlorobenzoyl)benzyl bromide

A refluxing mixture of 4-(2,6-dichlorobenzoyl)toluene (12.0 g, 45.2 mmol) and dibenzoylperoxide (90 mg, 0.37 mmol) in benzene (450 ml) was treated in portions with N-bromosuccinimide (8.83 g, 49.6 mmol), refluxed 1.5 hours, cooled, and evaporated to dryness under vacuum. The residue was triturated with diethyl ether (300 ml), filtered, and the filtrate was evaporated to dryness under vacuum. The crude product was chromatographed on a column of silica gel (700 g) eluted with 97:3 (v/v) hexaneethyl acetate to provide 7.49 g (48%) 4-(2,6-dichlorobenzoyl)benzyl bromide, m.p. 126°–130° C.

EXAMPLE 49

4-(2,6-Dichlorobenzoyl)benzyl azide

A mixture of 4-(2,6-dichlorobenzoyl)benzyl bromide (7.49 g, 21.8 mmol) and sodium azide (4.19 g, 64.5 mmol) in absolute ethanol (100 ml) was refluxed 5 hours, cooled, and evaporated under vacuum. The residue was triturated wit diethyl ether (100 ml), filtered, and evaporated under vacuum to provide 6.5 g (98%) 4-(2,6-dichlorobenzoyl)benzyl azide, m.p. 92°–94° C.

EXAMPLE 50

5-Amino-1-(4-[2,6-dichlorobenzoyl]benzyl)-1,2,3-triazole-4-carboxamide

A stirred, 65° C. mixture of sodium methoxide (330 mg, 6.11 mmol) in absolute ethanol (20 ml) was treated with 2-cyanoacetamide (527 mg, 6.27 mmol) and kept 10 minutes. The resulting suspension was treated with 4-(2,6-dichlorobenzoyl)benzyl azide (1.6 g, 5.2 mmol), refluxed 2 hours, cooled, treated with glacial acetic acid (600 μl, 629 mg, 10.5 mmol), and evaporated to dryness under vacuum. The residue was chromatographed on a column of silica gel (100 g) eluted with 19:1 (v/v) dichloromethane-methanol to provide 100 mg (5%) 5-amino-1-(4-[2,6-dichlorobenzoyl]benzyl)-1,2,3-triazole-4-carboxamide, m.p. 165°–167° C.

EXAMPLE 51

4-Chlorobenzoylmesitylene

A stirred 0° C. solution of mesitylene (7.21 g, 60.0 mmol) and 4-chlorobenzoyl chloride (10.55 g, 60.0 mmol) in carbon disulfide (130 ml) was treated with aluminum chloride (8.83 g, 66.1 mmol) in portions over 10 minutes. The mixture was stirred 75 minutes at 0° C., warmed to ambient temperature over 30 minutes, refluxed 10 hours, kept at ambient temperature 6 hours, cooled to 0° C., and quenched by addition of ice (250 g) and concentrated hydrochloric acid (50 ml). The mixture was extracted twice with diethyl ether and the combined extracts were washed with water (3X), saturated aqueous sodium carbonate, and brine, dried over anhydrous magnesium sulfate, and evaporated to dryness at 30° C. under vacuum. The residue was crystallized from methanol and dried to provide 9.61 g (62%) 4-chlorobenzoylmesitylene, m.p. 65.5°–66.5° C.

EXAMPLE 52

4-(4-Chlorobenzoyl)-3,5-dimethylbenzyl azide and 2-(4-chlorobenzoyl)-3,5-dimethylbenzyl azide A stirred, ambient temperature solution of 4-chlorobenzoylmesitylene (9.00 g, 34.8 mmol) in dry carbon tetrachloride (278 ml) was treated in one portion with a mixture of N-bromosuccinimide (6.19 g, 34.8 mmol) and benzoylperoxide (347 mg, 1.43 mmol). The mixture was refluxed 2 hours, cooled to ambient temperature, and filtered. The solids were washed well with carbon tetrachloride and the combined filtrate and washes were evaporated to dryness at 40° C. under vacuum. The residue was dissolved in dry dichloromethane (200 ml), stirred 2 hours at ambient temperature with tetramethylguanidinium azide (10.4 g, 66.0 mmol), and evaporated under vacuum. The residue was diluted with diethyl ether (300 ml), filtered, and the solid was washed well with diethyl ether. The combined filtrate and washes were extracted with water (2×300 ml) and brine (300 ml), dried over anhydrous magnesium sulfate, and evaporated to dryness at 30° C. under vacuum. The residue was chromatographed on silica gel (500 g) eluted with 1:1 (v/v) hexane-dichloromethane using a preparative high performance liquid chromatograph (HPLC) to provide 9.09 g of a mixture of azides. This mixture was chromatographed twice on silica gel (500 g) eluted with 93:7 (v/v) hexane-ethyl acetate using a preparative HPLC to provide 2.23 g (21%) oily 4-(4-chlorobenzoyl)-3,5-dimethylbenzyl azide (A) and 3.80 g (36%) oily 2-(4-chlorobenzoyl)-3,5-dimethylbenzyl azide (B).

A. IR (neat): 2100, 1675 cm$^{-1}$; 60 MHZ $^{1}$H NMR (CDCl$_3$): 2.16 s (6H), 4.33 s (2H), 7.04 s (2H), 7.40 dm (J=9 Hz, 2H), 7.74 dm (J=9 Hz, 2H).

B. IR (neat: 2105, 1670 cm$^{-1}$; 60 MHz $^{1}$H NMR (CDCl$_3$); 2.40 s (6H), 4.22 s (2H), 7.17 bs (1H), 7.21 bs (1H), 7.40 bd (J=8.5 Hz, 2H), 7.25 bd (J=8.5 Hz, 2H).

EXAMPLE 53

5-Amino-1-(4-[4-chlorobenzoyl]-3,5-dimethylbenzyl)-1,2,3-triazole-4-carboxamide

A stirred, 60° solution of sodium (105 mg, 4.55 mmol) in absolute ethanol (11.4 ml) was treated in one portion with 2-cyanoacetamide (382 mg, 4.55 mmol), kept 5 minutes, and treated in one portion with a solution of 4-(4-chlorobenzoyl)-3,5-dimethylbenzyl azide (1.05 g, 3.50 mmol) in absolute ethanol (4 ml). The mixture was refluxed 1 hour, cooled to ambient temperature, acidified with glacial acetic acid (577 μl, 605 mg, 9.10 mmol), and evaporated almost to dryness under vacuum. The residue was refluxed briefly with methanol (7 ml), cooled to ambient temperature, and filtered. The solid product was washed four times with small volumes of methanol, washed three times with water, and dried under vacuum at 40° C. to provide 870 mg (65%) 5-amino-1-(4-[4-chlorobenzoyl]-3,5-dimethylbenzyl)-1,2,3-triazole-4-carboxamide, m.p. 208°-209° C.

EXAMPLE 54

1-(4-Chlorobenzoyl)-2-chloro-4,6-dimethylbenzene and 1-(4-chlorobenzoyl)-4-chloro-2,6-dimethylbenzene A stirred, 0° C. solution of 1-chloro-3,5-dimethylbenzene (10.9 g, 77.2 mmol) and 4-chlorobenzoyl chloride (13.6 g, 77.2 mmol) in carbon disulfide (165 ml) was treated with aluminum chloride (11.4 g, 85.0 mmol) in portions over 15 minutes. The mixture was stirred 15 minutes at 0° C., 60 minutes at ambient temperature, 20 hours at reflux and 3 days at ambient temperature. The mixture was cooled to 0° C. and quenched by addition of ice (250 g) followed by concentrated hydrochloric acid (60 ml). The mixture was extracted twice with diethyl ether and the combined extracts were washed with water (3X), saturated aqueous sodium carbonate, and brine, dried over anhydrous magnesium sulfate, and evaporated to dryness of 30° C. under vacuum. The residue was chromatographed in three approximately equal batches on silica gel (500 g) eluted with 97:3 (v/v) hexane-ethyl acetate using a preparative high performance liquid chromatograph to provide 7.3 g (34%) 1-(4-chlorobenzoyl)-2-chloro-4,6-dimethylbenzene, m.p. 84°-87° C. [IR (neat): 2100, 1660 cm$^{-1}$; 60 MHz 'H NMR (CDCl$_3$): 2.11 s (3H), 2.34 s (3H), 6.94 bs (1H), 7.04 bs (1H), 7.34 dm (J=9 Hz, 2H), 7.70 dm (J=9 Hz, 2H)] and 3.4 g (16%) 1-(4-chlorobenzoyl)-4-chloro-2,6-dimethylbenzene, m.p. 41°-52° C. [IR (neat): 2100, 1660 cm$^{-1}$; 60 MHz 'H NMR (CDCl$_3$) 2.08 s (6H), 7.07 s (2H), 7.38 dm (J=9 Hz, 2H), 7.69 dm (J=9 Hz,2H)].

EXAMPLE 55

3-Chloro-4-(4-chlorobenzoyl)-5-methylbenzyl)azide and 3-chloro-2-(4-chlorobenzovl)-5-methylbenzyl azide A stirred, ambient temperature solution of 1-(4-chlorobenzoyl)-2-chloro-4,6-dimethylbenzene (6.90 g, 24.7 mmol) in dry carbontetrachloride (200 ml) was treated with N-bromosuccinimide (4.40 g, 24.7 mmol) and benzoylperoxide (250 mg, 1.03 mmol). The mixture was refluxed 4 hours, cooled to 0° C., and filtered. The precipitate was washed with carbon tetrachloride and the combined filtrate and wash were evaporated to dryness at 40° C. under vacuum. The oily residue was dissolved in dichloromethane (150 ml) treated with tetramethylguanidinium azide (8.1 g, 51.2 mmol), and stirred 20 minutes at ambient temperature. The solvent was evaporated under vacuum and the semisolid residue was triturated with diethyl ether (200 ml) and filtered. The solid was washed well with diethyl ether, and the combined filtrates and washes were extracted with water (2×150 ml) and brine (200 ml), dried over anhydrous magnesium sulfate, and evaporated to dryness under vacuum. The residue was triturated with hexane (400 ml), decanted, and evaporated under vacuum at 30° C. The residual oil was chromatographed on silica gel (500 g) eluted with 93:7 (v/v) hexane-ethyl acetate using a preparative high performance liquid chromatograph to provide 2.2 g (28%) oily 3-chloro-4-(4-chlorobenzoyl)-5-methylbenzyl azide [I.R. (neat): 2110, 1680 cm$^{-1}$; 60 MHz 'H NMR (CDCl$_3$): 2.17 (3H), 4.33 s (2H), 7.14 m (1H), 7.23 m (1H), 7.41 dm (J=9 Hz, 2H), 7.74 dm (J=9 Hz, 2H)] and 2.4 g (30%) oily 3-chloro-2-(4-chlorobenzoyl)-5-methylbenzyl azide [IR (neat): 2105, 1670 cm$^{-1}$; 60 MHz 'H NMR (CDCl$_3$): 2.39 s (3H), 4.23 s (2H), 7.17 s (1H), 7.21 s (1H), 7.40 dm (J=9 Hz, 2H), 7.75 dm (J=9Hz, 2 H)].

EXAMPLE 56

5-Amino-1-(3-chloro-4-[4-chlorobenzoyl]-5-methylbenzyl)-1,2,3-triazole-4-carboxamide A stirred, 60° C. solution of sodium (88.7 mg, 3.84 mmol) in absolute ethanol (9.6 ml) was treated with 2-cyanoacetamide (323 mg, 3.84 mmol), kept 5 min., and treated with 3-chloro-4-(4-chlorobenzoyl)-5-methylbenzyl azide (1.03 g, 3.20 mmol). The mixture was refluxed 1 hour, cooled to ambient temperature, acidified with glacial acetic acid (487 μl, 511 mg, 7.68 mmol), and evaporated to dryness at 30° C. under vacuum. The residue was chromatographed on a column of silica gel (150 g) eluted in 17 ml fractions with 19:1 (v/v) dichloromethane-methanol. Fractions 22–38 were combined and evaporated to dryness. The residual glass was kept 18 hours at ambient temperature with diethyl ether (25 ml), filtered, washed with diethyl ether, and dried to provide 870 mg (67%) crystalline 5-amino-1-(3-chloro-4-[4-chlorobenzoyl]-5-methylbenzyl)-1,2,3-triazole-4-carboxamide, m.p. 205°-206° C.

EXAMPLE 57

1-(4-Trifluoromethylbenzoyl)-2-chloro-4,6-dimethylbenzene and 1-(4-trifluoromethylbenzoyl)-4-chloro-2,6-dimethylbenzene A stirred, 0° C. solution of 3,5-dimethylchlorobenzene (16.4 g, 117 mmol) and 4-trifluoromethylbenzoyl chloride (24.4 g, 117 mmol) in carbon disulfide (250 ml) was treated in portions with aluminum chloride (17.1 g, 128 mmol). The mixture was stirred 30 minutes at 0° C., warmed to ambient temperature over 1 hour, refluxed 16 hours, and kept 3 days at ambient temperature. The mixture was cooled to 0° C., quenched by addition of ice-water (500 ml) and concentrated hydrochloric acid (100 ml), and extracted three times with diethyl ether. The combined extracts were washed with water (3×), 1N aqueous sodium hydroxide (2×250 ml), water (2×), and brine, dried over anhydrous magnesium sulfate, and evaporated to dryness under vacuum. The residue was multiply chromatographed on 500 g columns of silica gel eluted with 97:3 (v/v) hexane-ethyl acetate using a preparative high-performance liquid chromatograph to provide 6.90 g (17%) oily 1-(4-trifluoromethylbenzoyl)-2-chloro-4,6-dimethylbenzene (A) and 16.3 g oily 1-(4-trifluoromethylbenzoyl)-4-chloro-2,6-dimethylbenzene (B) contaminated with A.

A. 60 MHz 'H NMR (CDCl₃) 2.12 s (3H), 2.34 s (3H), 6.91 s (1H), 7.02 s (1H), 7.62 dm (J=8 Hz, 2H), 7.82 dm (J=8 Hz, 2H).

B. 60 MHz 'H NMR (CDCl₃): 2.10 s (6H), 7.08 s (2H), 7.68 dm (J=8 Hz, 2H), 7.90 dm (J=8 Hz, 2H).

EXAMPLE 58

4-(4-Trifluoromethylbenzoyl)-3-chloro-5-methylbenzyl azide and 2-(4-trifluoromethylbenzoyl)-3-chloro-5-methylbenzyl azide A stirred mixture of 1-(4-trifluoromethylbenzoyl)-2-chloro-4,6-dimethylbenzene (6.90 g, 22.1 mmol), N-bromosuccinimide (3.94 g, 22.1 mmol), and dibenzoyl peroxide (224 mg, 0.925 mmol) in dry carbon tetrachloride (180 ml) was refluxed 44 hours. Additional N-bromosuccinimide (1.97 g, 11.1 mmol) was added and the mixture was refluxed 24 hours. The mixture was cooled to 0° C., filtered, and washed with carbon tetrachloride. The combined filtrate and washes were evaporated to dryness under vacuum, and the residue was dissolved in dichloromethane (135 ml), treated with tetramethylguanidinium azide (7.25 g, 45.8 mmol), and stirred 40 minutes at ambient temperature. Solvent was removed under vacuum and the residue was stirred with diethyl ether (180 ml). The mixture was filtered and the precipitate was washed with diethyl ether. The combined filtrate and washes were washed twice with water and once with brine, dried over anhydrous magnesium sulfate, and evaporated to dryness under vacuum. The residue was dissolved in hexane (300 ml) and decanted, and the residual gum was washed with hexane. The combined hexane layers were evaporated to dryness under vacuum. The residue was chromatographed on silica gel (500 g) eluted with 93:7 (v/v) hexane-ethyl acetate using a preparative high-performance liquid chromatograph to provide 1.71 g (22%) oily 4-(4-trifluoromethylbenzoyl)-3-chloro-5-methylbenzyl azide (A), 1.30 g (17%) 2-(4-trifluoromethylbenzoyl)-3-chloro-5-methylbenzyl azide (B), and 0.48 g of a mixture of A and B.

A. IR (neat): 2110, 1680 cm⁻¹; 60 MHZ 'H NMR (CDCl₃) 2.21 s (3H), 4.39 s (2H), 7.17 s (1H), 7.25 s (1H), 7.68 dm (J=8 Hz, 2H), 7.95 dm (J=8 Hz, 2H).

B IR (neat): 2110, 1680 cm⁻¹; 60 MHz 'H NMR (CDCl₃); 2.41 s (3H), 4.24 s (2H), 7.18 s (1H), 7.22 s (1H), 7.67 dm (J=8 Hz, 2H), 7.92 dm (J=8 Hz, 2H).

EXAMPLE 59

5-Amino-1-(4-[4-trifluoromethylbenzoyl]-3-chloro-5-methylbenzyl)-1,2,3-triazole-4-carboxamide To a stirred, 60° C. solution of 2-cyanoacetamide (84.1 mg, 1.00 mmol) in absolute ethanol (3.0 ml) was added a solution of sodium hydroxide in methanol (0.80 ml of a 1.26 g/25 ml solution, 40 mg [1.0 mmol] NaOH). After 10 minutes at 60° C., a solution of 4-(4-trifluoromethyl]-3-chloro-5-methylbenzyl azide (354 mg, 1.00 mmol) in absolute ethanol (1.0 ml) was added, and the mixture was stirred at 60° C. for 20 minutes and at reflux for 75 minutes. Additional 2-cyanoacetamide (84.1 mg, 1.00 mmol) and a solution of sodium hydroxide in methanol (0.80 ml, 1.00 mmol NaOH) was added, and the mixture was refluxed 45 minutes. The mixture was cooled to ambient temperature, treated with glacial acetic acid (114 μl, 120 mg, 2.00 mmol), kept 24 hours, and evaporated to dryness. The residue was slurried with water (25 ml) containing glacial acetic acid (3 drops), filtered, washed with water and air dried. The residue was chromatographed on four 20 cm×20 cm 1500μ silica gel preparative thick-layer chromatography plates developed with 19:1 (v/v) dichloromethane/methanol. Product was eluted with 9:1 (v/v) dichloromethane-methanol, and the eluate was evaporated to dryness under vacuum. The residue was slurried with diethyl ether (2 ml), centrifuged, and washed with diethyl ether (3×1 ml). The solid residue was dried at 40° C. under vacuum to provide 207 mg (47%) 5-amino-1-(4-[4-trifluoromethylbenzoyl]-3-chloro-5-methylbenzyl)-1,2,3-triazole-4-carboxamide, m.p. 201°–201.5° C.

EXAMPLE 60

1-(4-[4-Trifluoromethylbenzoyl]-3-chloro-5-methylbenzyl)-5-methylamino-1,2,3-triazole-4-carboxamide A mixture of 5-amino-1-(4-[4-trifluoromethylbenzoyl]-3-chloro-5-methylbenzyl)-1,2,3-triazole-4carboxamide (438 mg, 1.00 mmole), methyl iodide (142 mg, 1.00 mmol), and potassium carbonate (138 mg, 1.00 mmole) in N,N-dimethylformamide (2.0 mL) is stirred 48 hours at ambient temperature, poured into water (15 mL), and filtered. Chromatography provides 1-4-[4-trifluoromethylbenzoyl]-3-chloro-5-methyl-benzyl)-5-methylamino-1,2,3-triazole-4-carboxamide.

What is claimed is:

1. A compound having the formula:

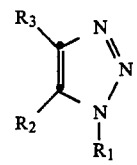

wherein:

$R_1$ is —$(CH_2)_p$—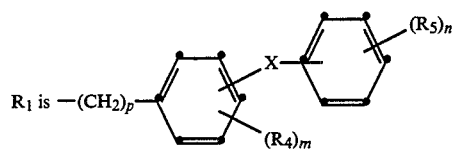

wherein p is 0 to 2; m is 0 to 4; and n is 0 to 5; X is O, S, SO, SO₂, CO, CHCN, CH₂ or C═NR₆ where R₆ is hydrogen, loweralkyl, hydroxy, loweralkoxy, amino, loweralkylamino, diloweralkylamino or cyano; and, $R_4$ and $R_5$ are independently halogen, cyano, trifluoromethyl, loweralkanoyl, nitro, loweralkyl, loweralkoxy, carboxy, lowercarbalkoxy, trifluoromethoxy, acetamido, loweralkylthio, loweralkylsulfinyl, loweralkylsulfonyl, trichlorovinyl, trifluoromethylthio, trifluoromethylsulfinyl, or trifluoromethylsulfonyl;

$R_2$ is amino, mono or diloweralkyl amino, acetamido, acetimido, ureido, formamido, formimido or guanidino; and $R_3$ is carbamoyl, cyano, carbazoyl, amidino or N-hydroxycarbamoyl;

wherein said loweralkyl, loweralkyl containing, lower alkoxy and loweralkanoyl groups contain from 1 to 3 carbon atoms.

2. The compound of claim 1 wherein p is 1; X is O, S, SO, SO₂, CO or C═NR₆ wherein R₆ is hydrogen, hydroxy, methoxy or cyano;

R₄ is fluoro, chloro, bromo, methyl, trifluoromethyl, cyano, carbomethoxy, trifluoromethoxy, trifluoromethylthio, or trichlorovinyl;

R₅ is halogen, methyl, trifluoromethyl, cyano, carbalkoxy, or trichlorovinyl;

R₂ is amino and

R₃ is carbamoyl.

3. The compound of claim 2 wherein p is 1; X is S, SO, SO₂, CO or C=NR₆ wherein R₆ is hydrogen, hydroxy, methoxy, or cyano;

R₄ is one or two substituents ortho to X and are independently fluoro, chloro, methyl, trifluoromethyl, cyano or carbomethoxy;

R₅ is 1 to 3 substituents meta and/or para to X and which are independently fluoro, chloro, methyl, cyano, carbomethoxy or trichlorovinyl;

R₂ is amino; and

R₃ is carbamoyl.

4. The compound of claim 1 which is 5-amino-1-[4-(4-chlorobenzoyl)-3-trifluoromethylbenzyl]-1,2,3-triazole-4-carboxamide.

5. The compound of claim 1 which is 5-amino-1-[4-(4-chlorobenzoyl)-3,5-dichlorobenzyl]-1,2,3-triazole-4-carboxamide.

6. The compound of claim 1 which is 5-amino-1-[4-(4-chlorophenylthio)-3,5-dichlorobenzyl]-1,2,3- triazole-4-carboxamide.

7. The compound of claim 1 which is 5-amino-1-[4-(4-chlorophenylsulfinyl)-3,5-dichlorobenzyl]-1,2,3-triazole-4-carboxamide.

8. The compound of claim 1 which is 5-amino-1-[4-(4-chlorobenzoyl)-3-chloro-5-methylbenzyl]-1,2,3-triazole-4-carboxamide.

9. The compound of claim 1 which is 5-amino-1-[4-(4-chlorobenzoyl)-3,5-dimethylbenzyl]-1,2,3 -triazole-4-carboxamide.

10. The compound of claim 1 which is 5-amino-1-[4-(4-trifluoromethylbenzoyl)-3-chloro-5-methylbenzyl]-1,2,3-triazole-4-carboxamide.

11. The compound of claim 1 which is 5-amino-1-[4-(3,4-dichlorobenzoyl)-3,5-dichlorobenzyl-1,2,3-triazole-4-carboxamide.

12. The compound of claim 1 which is 5-amino-1-(4-[1-(3-methylbenzimino)]-3,5-dichlorobenzyl)-1,2,3-triazole-4-carboxamide.

13. The compound of claim 1 which is 5-amino-1-[4-(4-fluorobenzoyl)-3-chloro-5-methylbenzyl]-1,2,3-triazole-4-carboxamide.

14. A method for preventing or treating coccidiosis in poultry which comprises administering to an animal in need of such treatment an effective amount of a compound of claim 1.

15. A composition useful for the prevention and treatment of coccidiosis in poultry which comprises an inert carrier and an effective amount of a compound of claim 1.

* * * * *